United States Patent
Moser et al.

(10) Patent No.: US 11,992,491 B2
(45) Date of Patent: May 28, 2024

(54) CRYSTALLINE SALTS OF 5-METHYL-(6S)-TETRAHYDROFOLIC ACID AND L-VALINE ETHYL ESTER

(71) Applicant: Merck Patent GmbH, Darmstadt (DE)

(72) Inventors: Rudolf Moser, Schaffhausen (CH); Viola Groehn, Dachsen (CH); Ruth Boehni Stamm, Stein Am Rhein (CH); Fritz Blatter, Reinach (CH); Martin Szelagiewicz, Basel (CH)

(73) Assignee: MERCK PATENT GMBH, Darmstadt (DE)

( * ) Notice: Subject to any disclaimer, the term of this patent is extended or adjusted under 35 U.S.C. 154(b) by 701 days.

(21) Appl. No.: 17/258,014

(22) PCT Filed: Jul. 2, 2019

(86) PCT No.: PCT/EP2019/067703
§ 371 (c)(1),
(2) Date: Jan. 5, 2021

(87) PCT Pub. No.: WO2020/007841
PCT Pub. Date: Jan. 9, 2020

(65) Prior Publication Data
US 2021/0275533 A1    Sep. 9, 2021

(30) Foreign Application Priority Data
Jul. 6, 2018 (EP) ..................... 18182281

(51) Int. Cl.
*A61K 31/519* (2006.01)
*A23L 33/00* (2016.01)
*A23L 33/10* (2016.01)
*A61K 31/223* (2006.01)

(52) U.S. Cl.
CPC ........... *A61K 31/519* (2013.01); *A23L 33/10* (2016.08); *A23L 33/40* (2016.08); *A61K 31/223* (2013.01); *A23V 2002/00* (2013.01)

(58) Field of Classification Search
None
See application file for complete search history.

(56) References Cited

U.S. PATENT DOCUMENTS

| 6,441,168 B1 | 8/2002 | Mueller et al. |
| 9,150,982 B2 | 10/2015 | Wang et al. |
| 2015/0018357 A1 | 1/2015 | Wang et al. |
| 2016/0207925 A1 | 7/2016 | Fracchia |

FOREIGN PATENT DOCUMENTS

| CN | 104356134 A | * | 2/2015 |
| CN | 104557937 A | | 4/2015 |

OTHER PUBLICATIONS

English translation of CN-104356134-A (2015).*
Vig et al. (Advanced Drug Delivery Reviews, 65:1370-1385 (2013).*
International Search Report dated Sep. 13, 2019 issued in corresponding PCT/EP2019/067703 application (3 pages).
English translation of Office Action in corresponding JP appln. No. 2021-500142 dated Jul. 11, 2023 (pp. 1-3).
English translation of First Office Action issued by the China National Intellectual Property Administration dated Jan. 5, 2023 in corresponding Chinese Application No. 201980044278.X (pp. 1-11).

* cited by examiner

*Primary Examiner* — Bong-Sook Baek
(74) *Attorney, Agent, or Firm* — Millen, White, Zelano & Branigan, P.C.; Brion P. Heaney

(57) ABSTRACT

The present invention refers to a crystalline salt comprising 5-methyl-(6S)-tetrahydrofolic acid and L-valine ethyl ester wherein the molar ratio of 5-methyl-(6S)-tetrahydrofolic acid and L-valine ethyl ester is from 1:0.3 to 1:3.0 (in mol/mol) and/or hydrates and/or solvates thereof as well as to a process of obtaining the same.

17 Claims, 3 Drawing Sheets

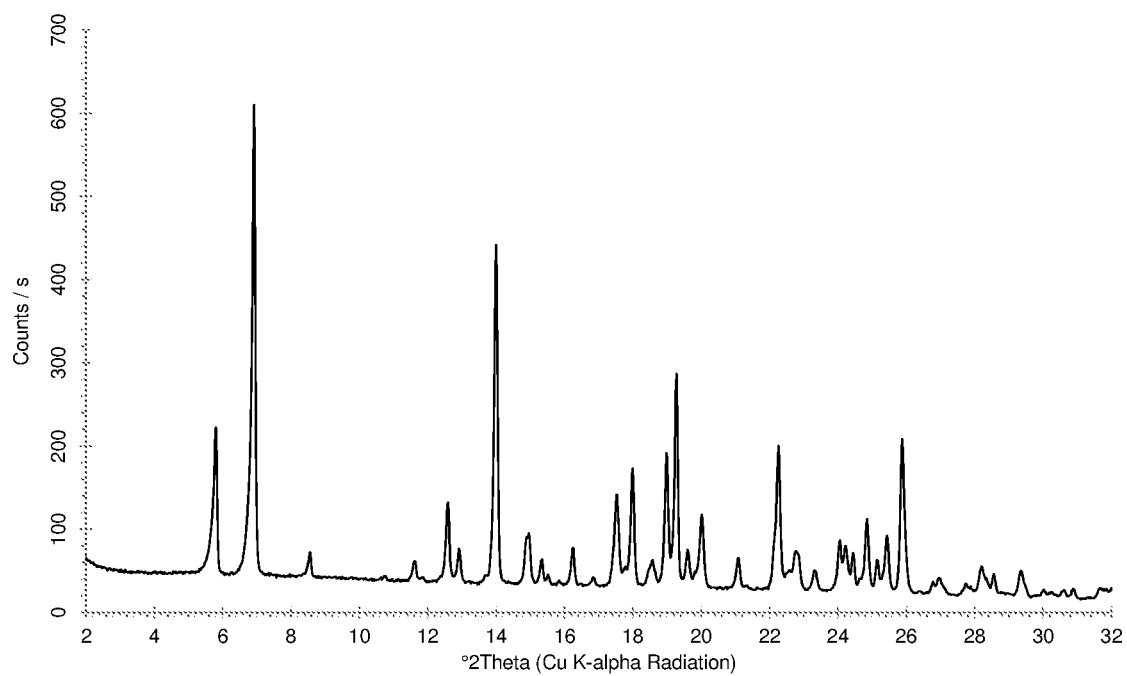
Figure 1: Powder X-ray diffraction pattern of the crystalline salt comprising 5-methyl-(6S)-tetrahydrofolic acid salt and L-valine ethyl ester 1:1 (Form A).

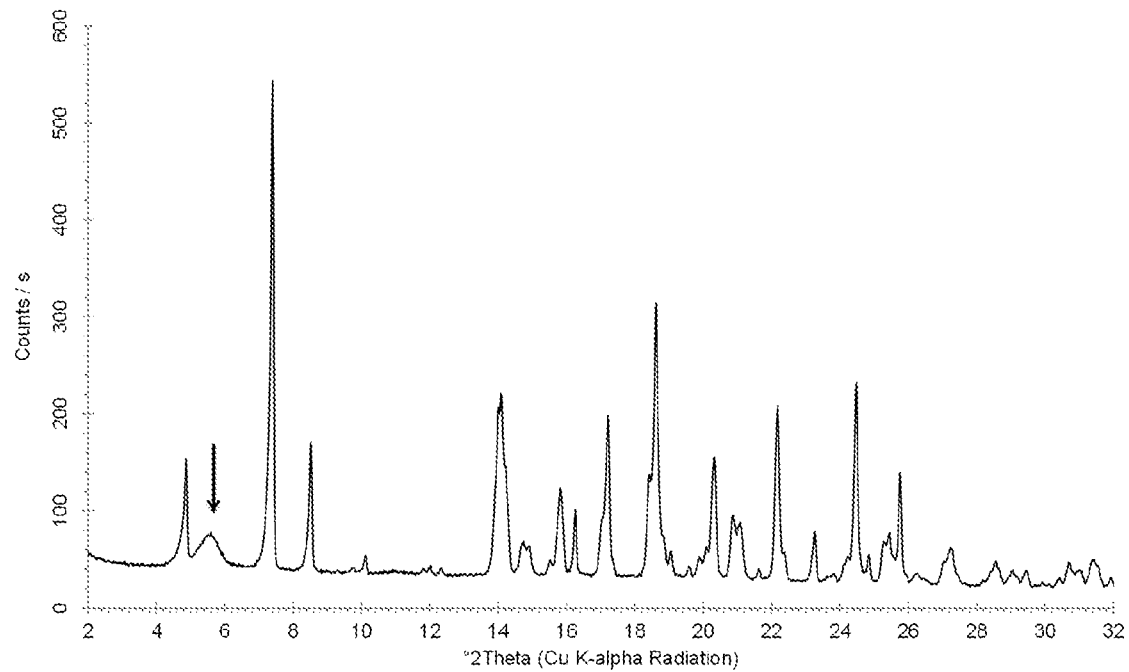
Figure 2: Powder X-ray diffraction pattern of the crystalline salt comprising 5-methyl-(6S)-tetrahydrofolic acid salt and L-valine ethyl ester 1:1 (Form B). The vertical arrow indicates a reflection from the Kapton foil.

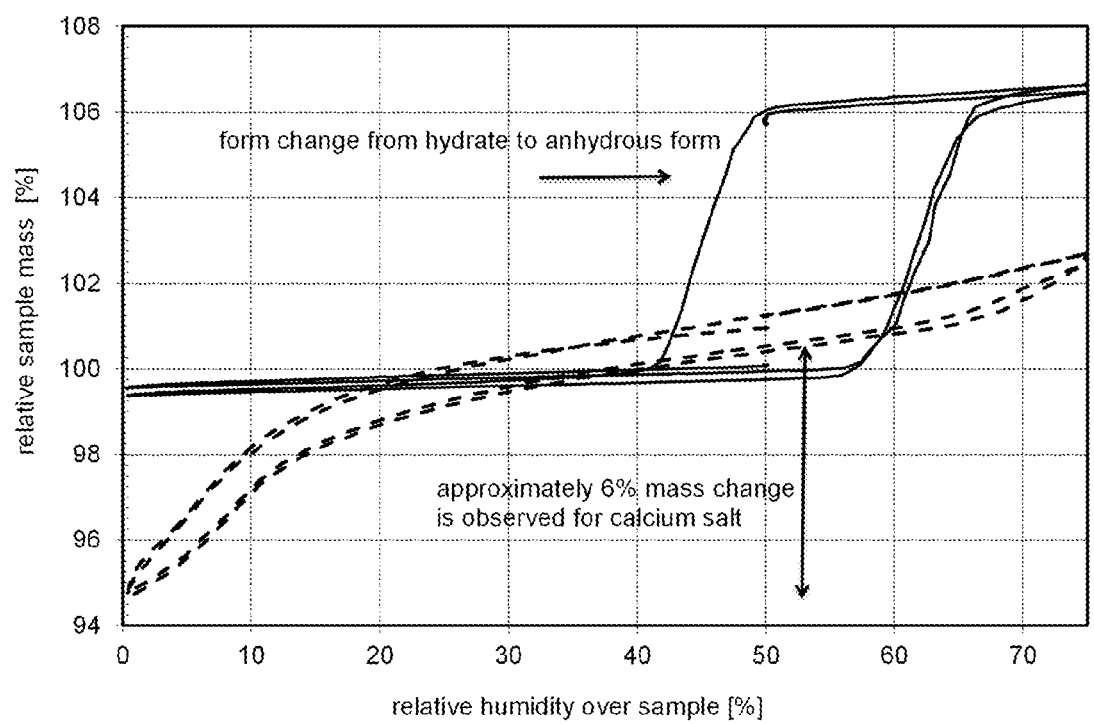
Figure 3: Dynamic water vapor sorption result for the crystalline salt comprising 5-methyl-(6S)-tetrahydrofolic acid and L-valine ethyl ester.

CRYSTALLINE SALTS OF 5-METHYL-(6S)-TETRAHYDROFOLIC ACID AND L-VALINE ETHYL ESTER

The present invention is directed to a crystalline salt comprising 5-methyl-(6S)-tetrahydrofolic acid and L-valine ethyl ester wherein the molar ratio of 5-methyl-(6S)-tetrahydrofolic acid to L-valine ethyl ester is from 1:0.3 to 1:3.0 (in mol/mol) and/or hydrates and/or solvates thereof.

Tetrahydrofolates are predominantly used as the calcium salt of 5-formyltetrahydrofolic acid (leucovorin and levoleucovorin), as the calcium salt of 5-methyltetrahydrofolic acid (Metafolin®), or as the sulfate salt of 5,10-methylenetetrahydrofolic acid (Modufolin®). Most prominent fields of use are for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

The calcium salt of 5-methyl-(6S)-tetrahydrofolic acid is used in particular as a drug and as a food additive, as a vitamin preparation, for the prevention of neural tube defects, for the treatment of depressive illnesses, and for influencing the homocysteine level.

5-Methyl-(6S)-tetrahydrofolic acid and salts thereof are known to be extremely unstable. In particular they are highly susceptible to oxidation [see also A. L. Fitzhugh, Pteridines 4 (4), 187-191 (1993) in this respect] and therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid and salts thereof.

U.S. Pat. No. 6,441,168 B1 discloses alkaline earth metal salts of 5-methyltetrahydrofolic acid, particularly the calcium salt, its crystallization and its use. The drawback of such crystalline calcium salt of 5-methyl-(6S)-tetrahydrofolic acid is that it exists in its crystalline form in up to four polymorphic modifications. Therefore, the process of manufacturing the crystalline calcium salt of 5-methyl-(6S)-tetrahydrofolic acid has to be controlled very precisely. Additionally, the crystalline calcium salt of 5-methyl-(6S)-tetrahydrofolic acid of U.S. Pat. No. 6,441,168 B1 typically contains in the crystal lattice of all its polymorphic forms at least one but up to four equivalents of water per equivalent of 5-methyl-(6S)-tetrahydrofolic acid.

US 2016207925 A1 is claiming lyophilised, spray-dried or boiled down compositions comprising L-asparagine or L-arginine together with 5-methyl-(6S)-tetrahydrofolic acid. However the disclosed compositions are simple, non-stochiometric mixtures and exist in an amorphous state.

New crystal forms of a pharmaceutically useful compound offer an opportunity to improve the performance profile of a pharmaceutical and/or vitamin/medical food products. It widens the reservoir of materials a formulation scientist has available for designing new dosage forms with improved characteristics.

The technical problem underlying the present invention is the provision of a crystalline form comprising 5-methyl-(6S)-tetrahydrofolic acid which overcomes the drawbacks of the crystalline calcium salt of 5-methyl-(6S)-tetrahydrofolic acid known in the art.

Additionally, new crystalline forms often show desired different physical and/or biological characteristics, which may assist in the manufacture or formulation of the active compound, to the purity levels and uniformity required for regulatory approval.

For the sake of stability of tetrahydrofolates it is always the aim to provide a compound which has a low water absorption upon storage and which can be dried sufficiently during manufacturing. In addition, drug substances that do not absorb high amounts of water under ambient conditions are highly desired. Particularly desired are substances that do not change their water content when the ambient relative humidity changes because large changes of the water content due to change of the relative humidity of the environment make it more difficult to achieve a great precision with the respect to the dosage form.

The technical problem is solved by a crystalline salt comprising 5-methyl-(6S)-tetrahydrofolic acid and L-valine ethyl ester wherein the molar ratio of 5-methyl-(6S)-tetrahydrofolic acid to L-valine ethyl ester is from 1:0.3 to 1:3.0 (in mol/mol) and/or hydrates and/or solvates thereof.

BRIEF DESCRIPTION OF THE DRAWING

FIG. 1 shows the powder X-ray diffraction pattern of the Form A crystalline salt comprising 5-methyl-(6S)-tetrahydrofolic acid salt and L-valine ethyl ester 1:1.

FIG. 2 shows the powder X-ray diffraction pattern of the Form B crystalline salt comprising 5-methyl-(6S)-tetrahydrofolic acid salt and L-valine ethyl ester 1:1, in which the vertical arrow indicates a reflection from the Kapton foil.

FIG. 3 shows the dynamic water vapor sorption result for the crystalline salt comprising 5-methyl-(6S)-tetrahydrofolic acid and L-valine ethyl ester.

The solid form of the present invention possesses improved pharmacological characteristics, thus offering enhanced possibilities to modulate and design improved drug products. Compared with the crystalline polymorphic forms of the calcium salt of 5-methyl-(6S)-tetrahydrofolic acid known in the art the water adsorption of the crystalline salt of 5-methyl-(6S)-tetrahydrofolic acid and L-valine ethyl ester is significantly lower leading to substantially improved control over the target dosage form level in the drug product because the change of the amounts of adsorbed water under changing relative humidity conditions is significantly less pronounced. Another advantageous aspect of the crystalline salt of 5-methyl-(6S)-tetrahydrofolic acid and L-valine ethyl ester is that a high chemical and optical purity of 5-methyl-(6S)-tetrahydrofolic acid can be achieved in one single crystallization step.

It is advantageous when a drug has a high kinetic solubility when orally administered leading to an improved and faster bioavailability. Consequently, the medicament can function more readily.

5-methyl-(6S)-tetrahydrofolic acid is poorly soluble in water. The thermodynamically stable form of the calcium salt (Form Ill) is known to exhibit an aqueous solubility of about 2.5 mg/ml and the solubility of the metastable Form I is about 10 mg/ml at room temperature. Under certain pH conditions, in particular when the pH of the environments is lower than the equilibrium pH of a given salt, the salts can potentially disproportionate into free acid and as a consequence, the solubility decreases substantially. Therefore, thermodynamic solubilities of the claimed salts at about neutral to lower pH values are inaccessible due to slow salt disproportionation (formation of poorly soluble free acid). However the bioavailability is dominated by kinetic effects. Administration of a solid form of a drug product is followed by dissolution and after the first dissolution step the drug is diluted by body fluids and distributed. Therefore the kinetic solubility is a key parameter that influences the bioavailability because the initially dissolved drug substance is readily diluted and transported. For the salt of 5-methyl-(6S)-tetrahydrofolic acid and L-valine was surprisingly found that the kinetic solubility is improved by about 50% versus the known (metastable Form 1) of the calcium salt. The difference in the kinetic solubility of the salt of the present invention to the thermodynamically stable form of the calcium salt (Form Ill) would presumably even be larger. Thus temporarily a much higher drug substance concentration can be achieved.

Preferably, the molar ratio of 5-methyl-(6S)-tetrahydrofolic acid to L-valine ethyl ester is from 1:0.5 to 1:2.5 (in mol/mol).

Even more preferred, the molar ratio of 5-methyl-(6S)-tetrahydrofolic acid to L-valine ethyl ester is from 1:0.75 to 1:1.25 (in mol/mol).

Most preferably, the ratio of 5-methyl-(6S)-tetrahydrofolic acid to L-valine ethyl ester is approximately 1:1 (in mol/mol) and/or hydrates and/or solvates thereof.

Preferably, the salt of the present invention is the crystalline salt of 5-methyl-(6S)-tetrahydrofolic acid and L-valine ethyl ester and has a PXRD pattern with at least one characteristic peak (expressed in 2θ±0.2° 2θ (CuKα radiation)) selected from the following peaks located at 5.8, 6.9, 14.0, 19.0, 19.3, 22.2 and 25.9 (Form A).

More preferred, the salt of the present invention is the crystalline salt of 5-methyl-(6S)-tetrahydrofolic acid and L-valine ethyl ester and has a PXRD pattern with at least three characteristic peak (expressed in 26±0.2° 2θ (CuKα radiation)) selected from the following peaks located at 5.8, 6.9, 14.0, 19.0, 19.3, 22.2 and 25.9 (Form A) and even more preferred, the salt of the present invention is the crystalline salt of 5-methyl-(6S)-tetrahydrofolic acid and L-valine ethyl ester and has a PXRD pattern with characteristic peaks (expressed in 26±0.2° 2θ (CuKα radiation)) at 5.8, 6.9, 14.0, 19.0, 19.3, 22.2 and 25.9 (Form A).

Even more preferred, the salt of the present invention is the crystalline salt of 5-methyl-(6S)-tetrahydrofolic acid and L-valine ethyl ester has a PXRD pattern with at least one characteristic peak (expressed in 26±0.2° 2θ (CuKα radiation)) selected from the following peaks located at 5.8, 6.9, 12.6, 14.0, 14.9, 17.5, 18.0, 19.0, 19.3, 20.0, 22.2 and 25.9 (Form A).

Most preferred, the salt of the present invention is the crystalline salt of 5-methyl-(6S)-tetrahydrofolic acid and L-valine ethyl ester and has a PXRD pattern substantially as shown in FIG. 1 (Form A).

Preferably, the salt of the present invention is the crystalline salt of 5-methyl-(6S)-tetrahydrofolic acid and L-valine ethyl ester and has a PXRD pattern with at least one characteristic peak (expressed in 26±0.2° 2θ (CuKα radiation)) selected from the following peaks located at 4.9, 7.4, 8.5, 14.1, 15.8, 16.3, 17.2, 18.6, 22.2 and 24.5 (Form B).

More preferred, the salt of the present invention is the crystalline salt of 5-methyl-(6S)-tetrahydrofolic acid and L-valine ethyl ester and has a PXRD pattern with at least three characteristic peaks (expressed in 26±0.2° 2θ (CuKα radiation)) selected from the following peaks located at 4.9, 7.4, 8.5, 14.1, 15.8, 16.3, 17.2, 18.6, 22.2 and 24.5 (Form B) and more preferred the salt of the present invention is the crystalline salt of 5-methyl-(6S)-tetrahydrofolic acid and L-valine ethyl ester and has a PXRD pattern with peaks (expressed in 26±0.2° 2θ (CuKα radiation)) at 4.9, 7.4, 8.5, 14.1, 15.8, 16.3, 17.2, 18.6, 22.2 and 24.5 (Form B).

Even more preferred, the salt of the present invention is the crystalline salt of 5-methyl-(6S)-tetrahydrofolic acid and L-valine ethyl ester and has a PXRD pattern with at least one characteristic peak (expressed in 26±0.2° 2θ (CuKα radiation)) selected from the following peaks located at 4.9, 7.4, 8.5, 14.1, 15.8, 17.2, 18.4, 18.6, 20.3, 20.9, 21.1, 22.2, 24.5 and 25.7 (Form B) and most preferred, the salt of the present invention is the crystalline salt of 5-methyl-(6S)-tetrahydrofolic acid and L-valine ethyl ester and has a PXRD pattern substantially as shown in FIG. 2 (Form B).

Even more preferred, the aforementioned crystalline salts have at least 99 wt % or more chemical and/or stereoisomerical purity.

A further aspect of the present invention is a process for obtaining the crystalline salt comprising 5-methyl-(6S)-tetrahydrofolic acid and L-valine ethyl ester comprising the steps of:

i) providing a mixture of 5-methyl-(6S)-tetrahydrofolic acid and L-valine ethyl ester, optionally in a suitable solvent or a mixture of solvents ii) adding a base, optionally in a suitable solvent or a mixture of solvents, to dissolve the compounds;

iii) heating the composition to at least 60° C. and optionally carrying out a clear filtration;

iv) crystallizing and cooling the mixture to a temperature between 1° C. and 30° C., optionally adding more solvent or mixture of solvents; and v) isolating the obtained solid material and optionally drying the product.

Preferably, the molar ratio of 5-methyl-(6S)-tetrahydrofolic acid and L-valine ethyl ester hydrochloride in step i) is in the range of from 1:1 to 1:3.

More preferred, the solvent is water.

In step iii) and/or iv) seed crystals may be added.

Preferably L-valine ethyl ester is used as L-valine ethyl ester hydrochloride.

Also, a pharmaceutical composition, food additive and/or preparation comprising the crystalline salt comprising 5-methyl-(6S)-tetrahydrofolic acid and L-valine ethyl ester and optionally one or more acceptable excipients is part of the present invention.

The pharmaceutical composition may be in the form of tablets, capsules, oral liquid preparations, powders, lyophilisates, granules, lozenges, reconstitutable powders, injectable or infusable solutions or suspensions or suppositories.

The pharmaceutical composition may further comprise at least one additional therapeutic agent and, preferably, is a pharmaceutical composition for oral, parenteral, intramuscular, intraspinal, intrathecal, periodontal, topical or rectal administration.

The use of the crystalline salt comprising 5-methyl-(6S)-tetrahydrofolic acid and L-valine ethyl ester as constituent for the production of drugs and/or as a food additive is also covered by the present invention.

The crystalline salt comprising 5-methyl-(6S)-tetrahydrofolic acid and L-valine ethyl ester can be used in the treatment in homocysteine-lowering, of anemia, neural tube defects, cardiovascular diseases, depression, cognitive impairment, Alzheimer's disease and osteoporosis and/or dietary management of low plasma and/or low red blood cell and/or low cerebrospinal fluid and/or low peripheral or central nervous system folate.

In summary, the profile of properties offered by the crystalline salt of 5-methyl-(6S)-tetrahydrofolic acid and L-valine ethyl ester of the present invention is advantageous for use in medicaments or as food additive. Especially, the low change in water content in an environment from 20% to 75% relative humidity could not been foreseen by the skilled artisan.

Moreover, the kinetic solubility is larger, what could also not had been foreseen by the skilled artisan.

EXAMPLES

Powder X-Ray Diffraction

Stoe Stadi P equipped with a Mythen1K Detector; Cu-Kα1 radiation; standard measurement conditions: transmission; 40 kV and 40 mA tube power; curved Ge monochromator; 0.02° 2θ step size, 48 s step time, 1.5-50.5° 2θ scanning range; detector mode: step scan; 1°2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

TG-FTIR

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

DVS

DVS measurements are typically performed with an SPS11-100n "Sorptions Prüfsystem" from ProUmid (formerly "Projekt Messtechnik"), August-Nagel-Str. 23, 89079 Ulm (Germany).

DVS measurements were conducted as follows: The sample was placed on an aluminum holder on top of a microbalance and allowed to equilibrate at 50% RH before starting the pre-defined humidity program:

(1) two hours kept at 50% constant relative humidity (RH) then
(2) raised RH to 95% at a rate of 5% per hour
(3) maintained RH at 95% for five hours
(4) reduced to 0% RH at a rate of 5% per hour
(5) maintained RH at 0% for five hours
(6) raised RH to 95% at a rate of 5% per hour
(7) maintained RH at 95% for five hours
(8) reduced to 0% RH at a rate of 5% per hour
(9) maintained RH at 0% for five hours
(10) raised to 50% RH at a rate of 5% per hour
(11) maintained RH at 50% for about one hour Example 1: Preparation of the Salt of 5-Methyl-(6S)-Tetrahydrofolic Acid and L-Valine-Ethyl Ester without Seeding 478 mg of 5-methyl-(6S)-tetrahydrofolic acid monohydrate was dissolved at room temperature in 2.00 mL of a 1.00 molar aqueous sodium hydroxide solution and 546 mg of L-valine ethyl ester hydrochloride was added. The solution was stirred at room temperature for about 20 minutes and 0.300 mL of a 1.00 molar aqueous hydrochloric acid solution was added. While stirring, the solution gradually changed into a concentrated suspension. 1.00 mL of water was added and the suspension was sonicated. An additional 0.300 mL of a 1 molar aqueous hydrochloric acid solution was added and the suspension again sonicated. The suspension was stirred at room temperature for about 70 minutes and the solid material was separated by centrifugal filtration under ambient conditions. 0.5 mL of water was added to the wet solid material in the filter centrifuge device and centrifugation was repeated. This wash step was repeated twice more using 0.50 mL and 1.00 mL of water, respectively. The wet filter cake was transferred into a fritted glass filter and air dried by drawing ambient air (about 22° C./about 34% r.h.) through the glass filter for about 20 minutes. The dried material was examined by $^1$H-NMR and identified as a 5-methyl-(6S)-tetrahydrofolic acid L-valine ethyl ester 1:1 salt. Analysis of the sample by TG-FTIR showed a water content of about 0.5%. Powder X-ray diffraction was carried out and the PXRD pattern of the L-valine ethyl ester salt Form A, substantially as depicted in FIG. 1 was obtained.

Example 2: Vacuum Drying of the Salt of 5-Methyl-(6S)-Tetrahydrofolic Acid and L-Valine Ethyl Ester About 112 mg of the crystalline material according to Example 1 was vacuum dried at room temperature and about 10 mbar for about one hour, followed by ventilation using ambient air (about 22° C./about 23% r.h.). Analysis of the sample by TG-FTIR showed a water content of about 0.3%.

An aliquot of the sample is prepared between two acetate foils for PXRD at room temperature and about 25% relative humidity. Powder X-ray diffraction was carried out and the PXRD pattern of the L-valine ethyl ester salt Form A, as depicted in FIG. 1 was obtained which exhibits peaks at 2-theta angles as listed in Table 1.

TABLE 1

2-theta angles, d-spacings and qualitative intensities for 5-methyl-(6S)-tetrahydrofolic acid L-valine ethyl ester salt Form A according to example 2. Vs = very strong, s = strong, m = medium, w = weak, and vw = very weak in intensity. It should be noted that intensity values can vary substantially due to preferred orientation effects.

| angle °2Θ | d-spacing [Å] | qualitative intensity |
| --- | --- | --- |
| 5.8 | 15.3 | s |
| 6.9 | 12.8 | vs |
| 8.5 | 10.3 | w |
| 10.7 | 8.2 | w |
| 11.6 | 7.6 | w |
| 11.9 | 7.5 | w |
| 12.6 | 7.0 | m |
| 12.9 | 6.9 | w |
| 14.0 | 6.3 | vs |
| 14.9 | 5.93 | m |
| 15.3 | 5.78 | w |
| 15.6 | 5.69 | w |
| 15.9 | 5.59 | w |
| 16.2 | 5.45 | w |
| 16.8 | 5.26 | w |
| 17.5 | 5.06 | m |
| 18.0 | 4.92 | m |
| 18.6 | 4.78 | w |
| 19.0 | 4.67 | s |
| 19.3 | 4.60 | s |
| 19.6 | 4.52 | w |
| 20.0 | 4.43 | m |
| 21.1 | 4.21 | w |
| 22.2 | 3.99 | s |
| 22.8 | 3.90 | w |
| 23.3 | 3.81 | w |
| 24.1 | 3.70 | w |
| 24.4 | 3.64 | w |
| 24.9 | 3.58 | m |
| 25.1 | 3.54 | w |
| 25.4 | 3.50 | m |
| 25.9 | 3.44 | s |
| 27.0 | 3.30 | w |
| 27.8 | 3.21 | w |

TABLE 1-continued 2-theta angles, d-spacings and qualitative intensities for 5-methyl-(6S)-tetrahydrofolic acid L-valine ethyl ester salt Form A according to example 2. Vs = very strong, s = strong, m = medium, w = weak, and vw = very weak in intensity. It should be noted that intensity values can vary substantially due to preferred orientation effects.

| angle °2Θ | d-spacing [Å] | qualitative intensity |
|---|---|---|
| 28.2 | 3.16 | w |
| 28.6 | 3.12 | w |
| 29.4 | 3.04 | w |

Example 3: Hydrate Formation of the Salt of 5-Methyl-(6S)-Tetrahydrofolic Acid and L-Valine Ethyl Ester About 100 mg of the crystalline material produced according to Example 1 was stored at room temperature and 75% relative humidity for 14 days. An aliquot of the sample was prepared for PXRD between two Kapton foils at room temperature and at about 55% relative humidity. Powder X-ray diffraction was carried out and the PXRD pattern of the L-valine ethyl ester salt Form B, as depicted in FIG. 2 was obtained which exhibits peaks at 2-theta angles as listed in Table 2.

TABLE 2

2-theta angles, d-spacings and qualitative intensities for 5-methyl-(6S)-tetrahydrofolic acid L-valine ethyl ester salt Form B according to Example 3. Vs = very strong, s = strong, m = medium, w = weak, and vw = very weak in intensity. It should be noted that intensity values can vary substantially due to preferredorientation effects.

| angle °2Θ | d-spacing [Å] | qualitative intensity |
|---|---|---|
| 4.9 | 18.2 | m |
| 5.6 | 15.9 | w |
| 7.4 | 12.0 | vs |
| 8.5 | 10.4 | s |
| 9.7 | 9.1 | w |
| 10.1 | 8.7 | w |
| 11.8 | 7.5 | w |
| 12.0 | 7.4 | w |
| 12.3 | 7.2 | w |
| 14.1 | 6.3 | s |
| 14.8 | 5.97 | w |
| 15.5 | 5.70 | w |
| 15.8 | 5.60 | m |
| 16.3 | 5.45 | m |
| 17.2 | 5.15 | s |
| 18.4 | 4.82 | m |
| 18.6 | 4.76 | s |
| 19.0 | 4.66 | w |
| 19.6 | 4.53 | w |
| 19.9 | 4.46 | w |
| 20.3 | 4.37 | m |
| 20.9 | 4.25 | m |
| 21.1 | 4.21 | m |
| 21.6 | 4.10 | w |
| 22.2 | 4.01 | s |
| 23.3 | 3.82 | w |
| 23.8 | 3.74 | w |
| 24.2 | 3.68 | w |
| 24.5 | 3.63 | s |
| 24.8 | 3.58 | w |
| 25.4 | 3.50 | w |
| 25.7 | 3.46 | m |
| 26.2 | 3.39 | w |
| 27.2 | 3.27 | w |
| 28.6 | 3.12 | w |
| 29.1 | 3.07 | w |
| 29.4 | 3.03 | w |
| 29.9 | 2.98 | vw |
| 30.4 | 2.94 | w |
| 30.7 | 2.91 | w |
| 31.0 | 2.88 | w |

Example 4: Preparation of the Salt of 5-Methyl-(6S)-Tetrahydrofolic Acid and L-Valine-Ethyl Ester 4.78 g of 5-methyl-(6S)-tetrahydrofolic acid monohydrate (assay 94.6%, [6S]-content 97.6%) were dissolved at room temperature in 20.0 mL of a 1.0 molar aqueous sodium hydroxide solution. 5.47 g of L-valine ethyl ester hydrochloride were added. To the solution then 3.0 mL of a 1.0 molar aqueous hydrochloric acid solution was added. While stirring, the solution gradually changed into a light suspension. Another 2.0 mL of a 1.0 molar aqueous hydrochloric acid solution was added in portions of 0.5 mL. The light suspension the was seeded with crystalline as obtained in Example 1. Another 1.0 mL of a 1.0 molar aqueous hydrochloric acid solution was added. The solid material was separated by filtration and washed with 3.0 mL water. The received solid was dried at 36° C./0-10 mbar. The dried material (2.61 g, corresponding to 43% assay corrected yield) was examined by PXRD and HPLC. The assay for 5-methyl-(6S)-tetrahydrofolic acid was 74.8% w/w. Powder X-ray diffraction pattern substantially as depicted in FIG. 1 (Form A) was obtained. HPLC disclosed a [6S]-content of 99.9%.

Example 5: Hygroscopicity and Water Content (DVS Experiments)

21 mg of the salt of 5-methyl-(6S)-tetrahydrofolic acid and L-valine ethyl ester according to Example 2 was weighed into an aluminum sample pan for DVS measurement. A DVS measurement was performed with an SPS11-100n "Sorptions Prufsystem" from ProUmid, August-Nagel-Str. 23, 89079 Ulm (Germany). For relative humidity (RH) scans, change rates of 5% per hour were used. The sample pan was placed into the instrument and a defined relative humidity change program was started according to the following steps:
  (1) Maintained RH for 2 hours at 50%, then
  (2) scanned RH from 50→0% at a rate of 5% per hour and maintained RH at 0% for 5 hours, then
  (3) scanned RH from 0→75% at a rate of 5% per hour and maintained RH at 75% for 5 hours, then
  (4) scanned RH from 75→0% RH at a rate of 5% per hour and maintained RH at 0% for 5 hours.
  (5) scanned RH from 0→75% at a rate of 5% per hour and maintained RH at 75% for 5 hours, then
  (6) scanned RH from 75→50% RH at a rate of 5% per hour and maintained RH at 50% for 2 hours.

In parallel, the very same protocol was applied to a sample of the calcium salt as a reference and the result is displayed in FIG. 3. Within the relative humidity range from 0 to 55% the relative sample mass for the salt of 5-methyl-(6S)-tetrahydrofolic acid and L-valine ethyl ester (solid line)

changes less than 1% while for the calcium salt (dashed line) the relative sample mass changes by about 6%.

Example 6: Kinetic Solubility of the Crystalline Salt of 5-Methyl-(6S)-Tetrahydrofolic Acid and L-Valine Ethyl Ester 42.5 mg of the anhydrous form of the crystalline 5-methyl-(6S)-tetrahydrofolic acid L-valine ethyl ester salt (Form A) according to Example 2 was weighed into a 7 mL glass vial with a screw cap. 2.00 mL of purified/de-ionized water (for instance water for chromatography) was added to the solid using an adjustable volumetric pipette. The mixture was vigorously agitated at room temperature for one minute. After one minute a dilute suspension was observed suggesting that most of the sample was dissolved. The dilute suspension was filtered by centrifugal filtration and 1.50 mL of the aqueous solution was transferred into a tared glass vial (about 10 mL volume). The water was evaporated in an air dryer at 40° C. for about 15 hours, then at 50° C. for about eight hours, subsequently drying was completed at 50° C. under vacuum (10 to 20 mbar) for about 13 hours. The solubility was determined by gravimetric evaluation of the solid residue. The solubility was 12.5 mg of 5-methyl-(6S)-tetrahydrofolic acid per mL.

Reference Example 1: Kinetic Solubility of the Calcium Salt of 5-Methyl-(6S)-Tetrahydrofolic Acid 42.5 mg of the anhydrous form of the crystalline 5-methyl-(6S)-tetrahydrofolic acid calcium salt was weighed into a 7 mL glass vial with a screw cap. 2.00 mL of purified/de-ionized water (for instance water for chromatography) was added to the solid using an adjustable volumetric pipette. The mixture was vigorously agitated at room temperature for one minute. After one minute a suspension was observed. The suspension was filtered by centrifugal filtration and 1.50 mL of the aqueous solution was transferred into a tared glass vial (about 10 mL volume). The water was evaporated in an air dryer at 40° C. for about 15 hours, then at 50° C. for about eight hours, subsequently drying was completed at 50° C. under vacuum (10 to 20 mbar) for about 13 hours. The solubility was determined by gravimetric evaluation of the solid residue. The solubility was 9.0 mg of 5-methyl-(6S)-tetrahydrofolic acid per mL.

The invention claimed is:

1. A crystalline salt comprising 5-methyl-(6S)-tetrahydrofolic acid and L-valine ethyl ester wherein the molar ratio of 5-methyl-(6S)-tetrahydrofolic acid to L-valine ethyl ester is from 1:0.3 to 1:3.0 (in mol/mol), or a hydrate or solvate thereof.

2. The crystalline salt of claim 1, wherein the molar ratio of 5-methyl-(6S)-tetrahydrofolic acid to L-valine ethyl ester is from 1:0.5 to 1:2.5 (in mol/mol), or a hydrate or solvate thereof.

3. The crystalline salt of claim 1, wherein the molar ratio of 5-methyl-(6S)-tetrahydrofolic acid to L-valine ethyl ester is from 1:0.75 to 1:1.25 (in mol/mol), or a hydrate or solvate thereof.

4. The crystalline salt of claim 1, wherein the ratio of 5-methyl-(6S)-tetrahydrofolic acid L-valine ethyl ester is approximately 1:1 (in mol/mol), or a hydrate or solvate thereof.

5. The crystalline salt of claim 1, wherein the crystalline salt of 5-methyl-(6S)-tetrahydrofolic acid and L valine ethyl and has a powder x-ray diffraction (PXRD) pattern with characteristic peaks, which are expressed in 2θ±0.2° 2θ with CuKα radiation, at 5.8, 6.9, 14.0, 19.0, 19.3, 22.2 and 25.9 (Form A).

6. The crystalline salt of claim 1, wherein the crystalline salt of 5-methyl-(6S)-tetrahydrofolic acid L valine ethyl ester has a PXRD pattern with characteristic peaks, which are expressed in 2θ±0.2° 2θ with CuKα radiation, at 4.9, 7.4, 8.5, 14.1, 15.8, 16.3, 17.2, 18.6, 22.2 and 24.5 (Form B).

7. The crystalline salt of claim 1 having at least 99 wt % or more chemical and/or stereoisomerical purity.

8. A process for obtaining the crystalline salt comprising 5-methyl-(6S)-tetrahydrofolic acid and L-valine ethyl ester according to claim 1 comprising the steps of: i) providing a mixture of 5-methyl-(6S)-tetrahydrofolic acid and L-valine ethyl ester, optionally in a suitable solvent or a mixture of solvents ii) adding a base, optionally in a suitable solvent or a mixture of solvents, to dissolve the compounds; iii) heating the resultant composition to at least 60° C. and optionally carrying out a clear filtration; iv) crystallizing and cooling the mixture to a temperature between 1° C. and 30° C., optionally adding more solvent or mixture of solvents; and v) isolating the obtained solid material and optionally drying the product.

9. The process of claim 8, wherein the molar ratio of 5-methyl-(6S)-tetrahydrofolic acid and L-valine ethyl ester in step i) is in the range of from 1:1 to 1:3.

10. The process of claim 8, wherein the solvent is water.

11. The process of claim 8, wherein in step iii) and/or step iv) seed crystals are added.

12. The process of claim 8, wherein L-valine ethyl ester is used as L-valine ethyl ester hydrochloride.

13. A pharmaceutical composition, food additive or preparation comprising the crystalline salt comprising 5-methyl-(6S)-tetrahydrofolic acid and L-valine ethyl ester, or, a hydrate or solvate thereof, according to claim 1 and optionally one or more acceptable excipients.

14. The pharmaceutical composition according to claim 13 wherein said composition is in the form of tablets, capsules, oral liquid preparations, powders, lyophilizates, granules, lozenges, reconstitutable powders, injectable or infusible solutions or suspensions, or suppositories.

15. The pharmaceutical composition according to claim 13 further comprising at least one additional therapeutic agent.

16. The pharmaceutical composition according to claim 13, wherein said composition is a pharmaceutical composition for oral, parenteral, intramuscular, intraspinal, intrathecal, periodontal, topical, or rectal administration.

17. A method of producing a drug formulation or food additive formulation comprising; combining a drug or food additive with the crystalline salt comprising 5-methyl-(6S)-tetrahydrofolic acid and L-valine ethyl ester, or a hydrate or solvate thereof, according to claim 1.

* * * * *